(12) United States Patent
Jordan

(10) Patent No.: US 9,220,674 B2
(45) Date of Patent: Dec. 29, 2015

(54) CATIONIC CONDITIONER REPLACEMENTS

(75) Inventor: Susan L. Jordan, Doylestown, PA (US)

(73) Assignee: Union Carbide Chemicals & Plastics Technology LLC, Midland, MI (US)

( * ) Notice: Subject to any disclaimer, the term of this patent is extended or adjusted under 35 U.S.C. 154(b) by 14 days.

(21) Appl. No.: 14/235,912

(22) PCT Filed: Sep. 14, 2012

(86) PCT No.: PCT/US2012/055389
§ 371 (c)(1),
(2), (4) Date: Jan. 29, 2014

(87) PCT Pub. No.: WO2013/048780
PCT Pub. Date: Apr. 4, 2013

(65) Prior Publication Data
US 2014/0205557 A1 Jul. 24, 2014

Related U.S. Application Data

(60) Provisional application No. 61/540,803, filed on Sep. 29, 2011.

(51) Int. Cl.
| | | |
|---|---|---|
| *A61Q 5/12* | (2006.01) | |
| *A61K 8/891* | (2006.01) | |
| *A61K 8/73* | (2006.01) | |
| *A61Q 5/02* | (2006.01) | |
| *A61K 8/58* | (2006.01) | |

(52) U.S. Cl.
CPC ............... *A61K 8/891* (2013.01); *A61K 8/585* (2013.01); *A61K 8/731* (2013.01); *A61Q 5/02* (2013.01); *A61Q 5/12* (2013.01); *A61K 2800/594* (2013.01)

(58) Field of Classification Search
CPC .......... A61Q 5/12; A61Q 5/02; A61K 8/891; A61K 8/731; A61K 2800/594; A61K 8/585
See application file for complete search history.

(56) References Cited

U.S. PATENT DOCUMENTS

| | | |
|---|---|---|
| 5,358,667 A | 10/1994 | Bergmann |
| 6,228,416 B1 | 5/2001 | Reibert et al. |
| 6,235,893 B1 | 5/2001 | Reibert et al. |
| 2005/0287087 A1 | 12/2005 | Huang et al. |
| 2010/0247459 A1 | 9/2010 | Drovetskaya et al. |
| 2014/0308227 A1* | 10/2014 | Mabille ............... 424/70.13 |

FOREIGN PATENT DOCUMENTS

| | | |
|---|---|---|
| EP | 0412710 A2 | 2/1991 |
| JP | 3765858 B2 | 4/2006 |
| JP | 2008001628 A | 1/2008 |
| WO | 2006007183 A1 | 1/2006 |
| WO | 2009/006212 A1 | 1/2009 |

OTHER PUBLICATIONS

Takeuchi, M. et al, "Rheological Properties of Reversible Thermo-Setting in Situ Gelling Solutions With the Methylcellulose-Polyethylene Glycol-Citric Acid Ternary System", Colloid & Polymer Science; Springer Verlag, Heidelberg, DE, vol. 281, No. 12, Apr. 2003, pp. 1178-1183.
Dow Chemicals: "Methocel Cellose Ethers—Technical Handbook", Internet Citation, Sep. 1, 2002, pp. 1-29, XP992629689. Retrieved from the Internet: URL: http://www.dow.com/dowwolff/en/pdfs/192-01062.pdf.
K. Engelskirchen,"Methyl Cellulose: Methylation of Alkali Cellulose With Methyl Chloride in Presense of Dimethyl Ether", Methoden der organischen Chemie; (Houben-Weyl), 4th ed., Bd. E20, 2063, Thieme Verlag, Stuttgart (1987).

* cited by examiner

*Primary Examiner* — Lezah Roberts
*Assistant Examiner* — Nannette Holloman
(74) *Attorney, Agent, or Firm* — Edward L. Brant

(57) ABSTRACT

Described are personal care compositions for hair, comprising a surfactant, a silicone, and a methylcellulose that gels at 45 C or less, wherein personal care composition is substantially free of cationic polymers selected from cationic cellulose derivatives, cationic guar derivatives, cationic methacrylamido polymers, polyquaternium-6, or polyquaternium-7.

9 Claims, No Drawings

CATIONIC CONDITIONER REPLACEMENTS

CROSS REFERENCE TO RELATED APPLICATIONS

This application is a 35 USC §371 national phase filing of PCT/US2012/055389 filed Sep. 14, 2012, which claims the benefit of U.S. Application No. 61/540,803, filed Sep. 29, 2011.

FIELD

The present invention relates to personal care compositions.

BACKGROUND

Some shampoos provide both cleansing and conditioning properties. Such conditioning shampoos require cationic polymers for enhanced deposition and film formation on the hair shaft, as well as aesthetic properties, such as wet comb and feel. Cationic polymers, however, can be associated with undesirable environmental effects, and tend to build up on hair after repeated use.

Accordingly, there exists in the market a need for enhanced conditioning in the absence of cationic polymers, while still having good aesthetic properties (tactile, visual, and the like), because aesthetic properties are of paramount importance in personal care.

DETAILED DESCRIPTION

In one embodiment, the present invention provides personal care compositions for hair, comprising a surfactant, a silicone, and a methylcellulose that gels at 45° C. or less, wherein personal care composition is substantially free of cationic polymers selected from cationic cellulose derivatives, cationic guar derivatives, cationic methacrylamido polymers, polyquaternium-6, or polyquaternium-7.

In some embodiments, the cationic polymer is any positively charged polymer.

The surfactant is a cationic, anionic, nonionic, or amphoteric surfactant, or a mixture thereof. In one embodiment, the surfactant is a nonionic/emulsifier surfactant. In one embodiment, the surfactant is a cationic surfactant, preferably behentrimonium chloride. In this embodiment, the surfactant is present in an amount from 0.1 wt % to 10 wt % by weight of the composition, preferably from 0.5 wt % to 7 wt % by weight of the composition, most preferably from 1 wt % to 4 wt % by weight of the composition.

In one embodiment, the surfactant is a detergent surfactant. In this embodiment, the surfactant is present in an amount from 1 wt % to 25 wt % by weight of the composition, preferably from 5 wt % to 20 wt % by weight of the composition, most preferably from 7 wt % to 18 wt % by weight of the composition.

Preferably, the detergent surfactant is an anionic surfactant in combination with an amphoteric surfactant. In one embodiment, the anionic surfactant is ammonium laureth sulfate, ammonium lauryl sulfate, sodium laureth sulfate, or sodium lauryl sulfate. In one embodiment, the anionic surfactant is present in an amount from 1 wt % to 25 wt %, preferably from 5 wt % to 20 wt %, more preferably from 7 wt % to 15 wt %, by weight of the composition.

In one embodiment, the mixture is an anionic surfactant in combination with a second surfactant that is disodium cocoamphodiacetate, decylglucoside, or cocamidopropyl betaine.

In one embodiment, the second surfactant is present in an amount from 1 wt % to 10 wt %, preferably from 1 wt % to 8 wt %, more preferably from 2 wt % to 6 wt %, by weight of the composition.

In a preferred embodiment, the surfactant is a mixture of sodium laureth sulfate (such as is commercially available from Cognis as under the tradename STANDAPOL ES) and disodium cocoamphodiacetate (such as is commercially available from Henkel as under the tradename VELVETEX CDC). When the surfactant is a mixture of sodium laureth sulfate and disodium cocoamphodiacetate, the ratio of sodium laureth sulfate to disodium cocoamphodiacetate is in a range from 9:1 to 2:1, most preferably 6:1.

Silicones include silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, 2-phenylethyltrimethyl siloxysilicates and polymethylphenylsiloxanes, fluoro oils such as partially hydrocarbon-based and/or partially silicone-based fluoro oils, preferably dimethicone, cyclopentasiloxane, cyclohexasiloxane, or a combination thereof. A preferred blend of dimethicone, Laureth-23, and C 12-15 Pareth-3 is commercially available from Dow-Corning under the tradename DOW CORNING 2-1491 Silicone Emulsion, also described as a 60% large particle size non-ionic emulsion of a blend of ultra-high molecular weight polydimethylsiloxane gum and intermediate molecular weight polydimethylsiloxane fluid. Preferably, the silicone is present in a range from 0.1 wt % to 5 wt %, preferably from 0.75 wt % to 3 wt %, and more preferably from 1 wt % to 2 wt %, by weight of the personal care composition.

One unusual property of methylcellulose is that it is known to exhibit reverse thermal gelation, in other words, methylcellulose gels at warmer temperatures and forms a liquid at cooler temperatures. Most grades of methylcellulose gel at around 50° C. to 60° C. A grade of methylcellulose that gels at a relatively low temperature, 38° C. to 44° C., is generally available under the tradename METHOCEL SG or SGA (The Dow Chemical Company). No grades of commercially available methylcellulose gel at temperatures as low as an individual's normal body temperature, however, U.S. Pat. No. 6,235,893, the entirety of which is incorporated by reference herein, teaches methylcelluloses that gel as low as 31° C.

In a preferred embodiment, the gelation is temperature-activated by a customer's body temperature, i.e., no crosslinker is required. In a preferred embodiment, the present methylcellulose is made according to the processes described in U.S. Pat. No. 6,235,893. U.S. Pat. No. 6,235,893 described lower gelation temperature as a desired and preferred but non-essential feature, (col. 3, lines 32-33).

In practice, the liquid should contain sufficient methylcellulose to induce the proper rate of gelation and strength of gel, as well as to achieve an initial viscosity (before imbibition) of at least 600 mPa·s, preferably at least 1000 mPa·s when measured at a shear rate of 10 sec-1. Accordingly, concentrations of methylcellulose in the liquid may understandably vary.

Methods of making methylcellulose are described in detail in U.S. Pat. No. 6,235,893. Generally, cellulose pulp is treated with a caustic, for example an alkali metal hydroxide. Preferably, 1 to 3.5 mol NaOH per mole of anhydroglucose units in the cellulose is used. Uniform swelling and alkali distribution in the pulp is optionally controlled by mixing and agitation. The rate of addition of aqueous alkaline hydroxide is governed by the ability to cool the reactor during the exothermic alkalization reaction. In one embodiment, an organic solvent such as dimethyl ether is added to the reactor as a diluent and a coolant. Likewise, the headspace of the reactor is optionally purged with an inert gas (such as nitrogen) to control oxygen-catalyzed depolymerization of the cellulose ether product. In one embodiment, the temperature is maintained at or below 45° C.

A methylating agent, such as methyl chloride or dimethyl sulfate, is also added by conventional means to the cellulose pulp, either before, after, or concurrent with the caustic, generally in an amount of 1.5 to 4 mol methylating agent per mole of anhydroglucose units in the cellulose. Preferably, the methylating agent is added after the caustic. Once the cellulose has been contacted with caustic and methylating agent, the reaction temperature is increased to 75° C. and reacted at this temperature for half an hour.

In a preferred embodiment, a staged addition is used, i.e., a second amount of caustic is added to the mixture over at least 60 minutes, preferably at least 90 minutes, while maintaining the temperature at least 55° C., preferably a least 65° C., more preferably at least 80° C. Preferably, 2 to 4 mol caustic per mole of anhydroglucose units in the cellulose is used. A staged second amount of methylating agent is added to the mixture, either before, after, or concurrent with the caustic, generally in an amount of 2 to 4.5 mol methylating agent per mole of anhydroglucose units in the cellulose.

The cellulose ether is washed to remove salt and other reaction by-products. Any solvent in which salt is soluble may be employed, but water is preferred. The cellulose ether may be washed in the reactor, but is preferably washed in a separate washer located downstream of the reactor. Before or after washing, the cellulose ether may be stripped by exposure to steam to reduce residual organic content.

The cellulose ether is dried to a reduced moisture and volatile content of preferably 0.5 to 10.0 weight percent water and more preferably 0.8 to 5.0 weight percent water and volatiles based upon the weight of cellulose ether. The reduced moisture and volatiles content enables the cellulose ether to be milled into particulate form. The cellulose ether is milled to particulates of desired size. If desired, drying and milling may be carried out simultaneously.

Other optional ingredients for personal care compositions of the present invention include cosmetically acceptable emollients, sunscreens, surfactants, emulsifiers, preservatives, rheology modifiers, colorants, dyes, preservatives, pH adjustors, propellants, reducing agents, fragrances, foaming agents, tanning agents, depilatory agents, flavors, astringents, antiseptics, deodorants, antiperspirants, insect repellants, bleaches, tighteners, anti-dandruff agents, adhesives, polishes, strengtheners, fillers, barrier materials, or biocides.

The amount of optional ingredients effective for achieving the desired property provided by such ingredients can be readily determined by one skilled in the art.

In one embodiment, the personal care composition may be formulated in the form of a leave-on hair composition, containing a moisturizer, conditioner, and/or styling active.

In one embodiment, the personal care composition may be formulated in the form of a skin care composition, such as a lotion or cream, containing a moisturizer, anti-aging, and/or suncare active. In one embodiment, the personal care composition may be formulated in the form of a skin care composition, such as a mask.

EXAMPLES

The following examples are for illustrative purposes only and are not intended to limit the scope of the present invention. All percentages are by weight unless otherwise specified.

Example 1

An example of a personal care composition of the present invention is listed in TABLE 1, in wt %:

TABLE 1

|  | Batch A |
| --- | --- |
| DI water | 14.70 |
| Sodium Laureth Sulfate | 60.78 |
| Disodium Cocoamphodiacetate | 6.92 |
| Ethyleneglycol distearate (EDGS) | 2.0 |
| DC 1664 Silicone emulsion trimethyl-trimethylsilyloxy-silane (50%) | 2.0 |
| SGA7C Methylcellulose (The Dow Chemical Company); gelation temperature ~45° C. | 15.0 |
| GLYDANT DMDM Hydantoin | 0.4 |
| Citric acid (10%) | 2.2 |

To prepare the formulation, the DI water is heated to 80-90° C., and SGA7C methylcellulose powder sprinkled in and stirred. Once a consistent dispersion is formed, reduce the temperature to 70-75° C., add surfactants. Next, add EGDS and stir at 500 rpm for 15 minutes at 70-75° C. Cool to 35° C. and increase stirrer to 750 rpm and slowly add DC 1664; stir for 15 minutes. Add 10% citric acid and stir 10 minutes. Add Glydant preservative and sufficient water to reach 100 g. Stir 15 minutes at approximately 500 rpm.

Example 2

Comparative

Comparative personal care compositions are listed in TABLE 2, in wt %:

TABLE 2

|  | Comparative Batch 1 | Comparative Batch 2 |
| --- | --- | --- |
| DI water | 14.70 | 4.70 |
| Sodium Laureth Sulfate | 60.78 | 60.78 |
| Disodium Cocoamphodiacetate | 6.92 | 6.92 |
| Ethyleneglycol distearate (EDGS) | 2.0 | 2.0 |
| DC 1664 Silicone emulsion trimethyl-trimethylsilyloxy-silane (50%) | 2.0 | 2.0 |
| A4M Methylcellulose (The Dow Chemical Company); gelation temperature ~65° C. | 15.0 | 15.0 |
| Polyquaternium-10 cationic polymer | — | 10.0 |
| GLYDANT DMDM Hydantoin | 0.4 | 0.4 |
| Citric acid (10%) | 2.2 | 2.2 |

Formulations are prepared substantially according to Example 1.

Example 3

To test Batch A and Comparative Batch 1, compositions substantially according to the protocols of Examples 1 and 2 were prepared. Pre-washed and pre-hydrated tresses of European Virgin-Brown and 8-hour bleached hair (available from International Hair Importers and Products Inc.) were treated with 1.0 g of these shampoo formulations as described below. The shampoo was worked into the hair for 1 min and then rinsed off under running tap water at 38° C. at 0.4 gal./min. water flow.

The hair tresses were hung for wet sensory evaluation study. After the tresses were completely dried, dry sensory evaluations were conducted. Expert panelists trained to evaluate the performance of cosmetic products on hair were asked to evaluate comb-ability and feel in both the wet and dry stage. Each panelist evaluated a pair of tresses, one tress treated with a composition of the invention versus one treated with a comparative composition. The panelists were asked to pick one tress with superior wet and dry attributes. Virgin brown hair results are given in TABLE 3.

TABLE 3

|  | Batch A | Comparative Batch 1 |
|---|---|---|
| Wet comb | 70 | 30 |
| Wet feel | 70 | 30 |
| Dry comb | 70 | 30 |
| Dry feel | 70 | 30 |

The results show an improvement in wet combing benefit in Batch A samples.

Objective wet combing measurements were taken using a DIA-STRON device from Dia-Stron Limited, Hampshie, UK on bleached hair. The lower force required to pull the comb through the hair, the more conditioned the hair is. Batch A showed a significant reduction in combing force (43% reduction in friction) compared to Comparative Batch 1 (13% reduction in friction).

In a separate evaluation, the amount of silicone deposited on hair after shampooing was measured. Five grams of hair was washed with 1 gram of a shampoo, and rinsed at constant temperature. Each tress was washed five times before extraction. Hair was extracted with a 1:1 mixture of methyl butyl ketone and toluene. Each hair tress is washed 5 times with the formulations and allowed to dry between washes. Atomic absorption spectroscopy was used to measure silicone content; reporting μg silicone/g hair. Each sample is run in triplicate. There was no change in silicone deposition between Batch A and Comparative Batch 1, suggesting the increased level of conditioning performance is not due to enhanced silicone deposition. Without wishing to be bound by theory, it is possible when the shampoo comes in contact with the hair, the lower gel temperature may cause the polymer to "gel" during the wash step, resulting in deposition.

The invention claimed is:

1. A cleansing and conditioning personal care composition for hair, comprising:
    a surfactant;
    a silicone; wherein the silicone is dimethicone; and
    a methylcellulose that gels at 45° C. or less, and wherein the methylcellulose ether is present in a range from 0.1 wt % to 10 wt % by weight of the personal care composition.

2. The personal care composition of claim 1, wherein the methylcellulose ether is present in a range from 0.25 wt % to 5.0 wt %.

3. The personal care composition of claim 1, wherein the surfactant is a detergent surfactant.

4. The personal care composition of claim 1, wherein the surfactant is a mixture of sodium laureth sulfate and disodium cocoamphodiacetate.

5. The personal care composition of claim 4, wherein the dimethicone is present in a range from 0.1 wt % to 5 wt %.

6. The personal care composition of claim 1, wherein the surfactant is a nonionic surfactant.

7. A method of conditioning hair, comprising applying the personal care composition of claim 1 to hair.

8. The method of claim 7, wherein silicone deposition not increased.

9. The method of claim 7, wherein combability is increased.

* * * * *